(12) United States Patent
Maharshi Ramaswamy et al.

(10) Patent No.: US 10,160,080 B2
(45) Date of Patent: Dec. 25, 2018

(54) SKIN SENSING USING SPECTRAL ANALYSIS

(71) Applicant: Robert Bosch GmbH, Stuttgart (DE)

(72) Inventors: Bharadwaja Maharshi Ramaswamy, Bangalore (IN); Yeshwanth Sampangi Ramaiah, Bangalore (IN); Vishwanatha Manevarthe Srikantiah, Bangalore (IN)

(73) Assignees: Robert Bosch Tool Corporation, Broadview, IL (US); Robert Bosch GmbH, Stuttgart (DE)

( * ) Notice: Subject to any disclaimer, the term of this patent is extended or adjusted under 35 U.S.C. 154(b) by 239 days.

(21) Appl. No.: 15/104,079

(22) PCT Filed: Dec. 12, 2014

(86) PCT No.: PCT/EP2014/077505
§ 371 (c)(1),
(2) Date: Jun. 13, 2016

(87) PCT Pub. No.: WO2015/091245
PCT Pub. Date: Jun. 25, 2015

(65) Prior Publication Data
US 2016/0318142 A1 Nov. 3, 2016

(30) Foreign Application Priority Data
Dec. 18, 2013 (IN) .......................... 5929/CHE/2013

(51) Int. Cl.
*B23Q 11/00* (2006.01)
*F16P 3/14* (2006.01)
(Continued)

(52) U.S. Cl.
CPC ...... *B23Q 11/0082* (2013.01); *B23Q 17/2438* (2013.01); *B27G 19/02* (2013.01);
(Continued)

(58) Field of Classification Search
CPC ............ B23Q 11/0082; B23Q 17/2438; B23Q 17/24; G01N 21/35; G01N 2201/062;
(Continued)

(56) References Cited

U.S. PATENT DOCUMENTS

| | | | | |
|---|---|---|---|---|
| 8,091,456 B2 * | 1/2012 | Keller | .................... | B27G 19/02 83/477.2 |
| 8,113,097 B2 * | 2/2012 | Marx | .................... | B23Q 11/06 192/129 R |
| 8,386,067 B2 * | 2/2013 | Krapf | ................. | B23Q 11/0082 700/174 |
| 8,575,549 B2 * | 11/2013 | Visel | ................. | B23Q 11/0082 250/338.1 |

(Continued)

FOREIGN PATENT DOCUMENTS

DE 10 2008 002 431 A1 12/2008
DE 10 2007 044 800 A1 4/2009
(Continued)

OTHER PUBLICATIONS

International Search Report corresponding to PCT Application No. PCT/EP2014/077505, dated Mar. 10, 2015 (4 pages).
(Continued)

*Primary Examiner* — Ghassem Alie
(74) *Attorney, Agent, or Firm* — Maginot Moore & Beck LLP

(57) ABSTRACT

A power tool includes a moving implement, implement arrest mechanism, light emitters, photodetector, and controller. The controller activates a first emitter to direct light with a wavelength between 800 nm and 1100 nm on an object and identifies a first reflectance level of the object from a reflectance signal from the photodetector. The controller activates a second emitter to direct light with a wavelength between 1350 nm and 1800 nm on the object and identifies a second reflectance level of the object from the photodetector. The controller activates the implement arrest mechanism to prevent contact between the object and the moving implement if a ratio corresponding to the first identified reflectance level and the second identified reflectance level exceeds a predetermined threshold.

8 Claims, 7 Drawing Sheets

(51) Int. Cl.
*B27G 19/02* (2006.01)
*G01N 21/35* (2014.01)
*B23Q 17/24* (2006.01)

(52) U.S. Cl.
CPC ............... *F16P 3/14* (2013.01); *F16P 3/142* (2013.01); *F16P 3/144* (2013.01); *G01N 21/35* (2013.01); *G01N 2201/062* (2013.01)

(58) Field of Classification Search
CPC . F16P 3/14; F16P 3/144; Y10T 83/533; Y10T 83/081; Y10T 83/089; Y10T 83/091; Y10T 83/773; B27G 19/02
USPC ........ 83/58, 62.1, 561, 47, 63, 74, 469, 788, 83/DIG. 1, 477.2, 477.1, 490, 589, 471.3, 83/397.1, 297; 144/382, 427; 173/1; 700/21, 171, 108; 702/65; 340/686.5, 340/411; 307/117; 241/37.5; 320/166, 320/562, 658, 663, 665, 667, 666, 668, 320/675, 686, 688, 698; 361/181, 281, 361/286, 176; 250/342; 424/9.5, 9.6
See application file for complete search history.

(56) References Cited

U.S. PATENT DOCUMENTS 9,862,097 B2 * 1/2018 Melikian ................. G01B 11/14
2006/0101960 A1 * 5/2006 Smith .................. B23D 59/001
83/58
2010/0212466 A1 * 8/2010 Stellmann .......... B23Q 11/0082
83/63

FOREIGN PATENT DOCUMENTS

DE 10 2008 002 503 A1 12/2009
DE 10 2009 045 322 A1 4/2011
WO 2008/071805 A1 6/2008

OTHER PUBLICATIONS

Nunez, Abel S., A Physical Model of Human Skin and Its Application for Search and Rescue; Doctoral Dissertation; Dec. 1, 2009; 205 Pages; Air Force Institute of Technology, Ohio, USA; available at: http://www.dtic.mil/dtic/tr/fulltext/u2/a511354.pdf.

* cited by examiner

SKIN SENSING USING SPECTRAL ANALYSIS

CLAIM OF PRIORITY

This application is a 35 U.S.C. § 371 National Stage Application of PCT/EP2014/077505, filed on Dec. 12, 2014, which claims the benefit of priority to Indian Provisional Application No. 5929/CHE/2013, which is entitled "Skin Sensing Using Spectral Analysis" and was filed on Dec. 18, 2013, the entire contents of which are hereby incorporated by reference herein.

TECHNICAL FIELD

This disclosure relates generally to power tools, and, more specifically, to systems and methods for detecting proximity between a human and a moving implement in a power tool.

BACKGROUND

Detection or sensing systems have been developed for use with various kinds of manufacturing equipment and power tools. Such detection systems are operable to trigger a reaction device by detecting or sensing the contact of some appendage of an operator with some part of the equipment. For example, capacitive contact sensing systems in table saws that are known to the art detect contact between the operator and the blade, and a reaction device, such as a brake or blade withdrawal device, either halts motion of the blade or removes the blade from contact with the human.

Existing detection systems are generally configured to identify contact between a moving part of the power tool, such as a saw blade, and an appendage or other part of the human body before halting the motion of the blade. The existing systems detect either direct contact with the human appendage, or extreme proximity to the human appendage through capacitive coupling at distances of no more than a few millimeters. Given the minimal detection distances, the existing systems often require high-precision mechanisms to halt a moving saw blade or other implement in a very short time period, such as within 1 millisecond. In light of these deficiencies, improvements to detection systems that enable identification of potential contact between a human appendage and a moving implement in a power tool without requiring direct contact between the appendage and implement would be beneficial.

SUMMARY

In one embodiment, a power tool has been developed. The power tool includes an implement, an actuator configured to move the implement during operation of the power tool, an implement arrest mechanism, a first emitter configured to emit light at a wavelength between 800 nm and 1100 nm, a second emitter configured to emit light at a wavelength between 1350 nm and 1800 nm, a photodetector configured to receive a reflection signal from an object that receives the light from the first emitter and the second emitter, and a controller operatively connected to the actuator, the implement arrest mechanism, the first emitter, the second emitter, and the photodetector. The controller is configured to operate the actuator to move the implement, activate only the first emitter, identify a first reflectance level from the object with reference to a first reflection signal received by the photodetector when only the first emitter is activated, activate only the second emitter, identify a second reflectance level from the object with reference to a second reflection signal received by the photodetector when only the second emitter is activated, and activate the implement arrest mechanism to prevent contact between the object and the implement while the implement is in motion in response to a ratio corresponding to the first identified reflectance level and the second identified reflectance level exceeding a first predetermined threshold.

In another embodiment, a method of operating a power tool has been developed. The method includes operating an actuator to move an implement, activating with a controller only a first emitter to emit light at a wavelength between 800 nm and 1100 nm, identifying with the controller a first reflectance level from an object with reference to a first reflection signal received by a photodetector when only the first emitter is activated, activating with the controller only a second emitter to emit light at a wavelength between 1350 nm and 1800 nm, identifying with the controller a second reflectance level from an object with reference to a first reflection signal received by the photodetector when only the second emitter is activated, and activating with the controller an implement arrest mechanism to prevent contact between the object and the implement while the implement is in motion in response to a ratio corresponding to the first identified reflectance level and the second identified reflectance level exceeding a first predetermined threshold.

DETAILED DESCRIPTION

For the purposes of promoting an understanding of the principles of the embodiments described herein, reference is now made to the drawings and descriptions in the following written specification. No limitation to the scope of the subject matter is intended by these references. This patent also encompasses any alterations and modifications to the illustrated embodiments as well as further applications of the principles of the described embodiments as would normally occur to one skilled in the art to which this document pertains.

As used herein, the term "power tool" refers to any tool with one or more moving parts that are moved by an actuator, such as an electric motor, an internal combustion engine, a hydraulic or pneumatic cylinder, and the like. For example, power tools include, but are not limited to, bevel saws, miter saws, table saws, circular saws, reciprocating saws, jig saws, band saws, cold saws, cutters, impact drives, angler grinders, drills, jointers, nail drivers, sanders, trimmers, and routers. As used herein, the term "implement" refers to a moving part of the power tool that is at least partially exposed during operation of the power tool. Examples of implements in power tools include, but are not limited to, rotating and reciprocating saw blades, drill bits, routing bits, grinding disks, grinding wheels, and the like. As described below, a monitoring system identifies the skin of human operator and activates an implement arrest mechanism to halt the implement or withdraw the implement prior to contact with the human operator.

As used herein, the term "implement arrest mechanism" refers to a range of devices including brakes and retraction mechanisms that stop a moving implement, retract the moving implement from a location where the implement can contact a human operator, or both. For example, a blade brake mechanism in a saw stops the motion of a moving blade in a short period of time. A blade drop or blade retraction device moves the blade out of a position where the blade can contact a human operator. In a table saw embodiment, a blade drop system pulls a moving blade below the level of the table in the table saw to prevent contact between the blade and the operator. The blade retraction system optionally includes a blade brake mechanism as well.

As used herein, the term "light" refers to a form of electromagnetic radiation in the infrared, visible light, and ultraviolet spectra. As described in more detail below, light emitters, such as light emitting diodes or other electromagnetic emitters, generate light at different wavelengths including infrared radiation wavelengths, visible light wavelengths, and ultraviolet light wavelengths. A power tool identifies the reflectance levels of light that an emitter produces at different wavelengths to identify human skin or other objects such as work pieces that are in an area around an implement in the tool.

Figure 1:
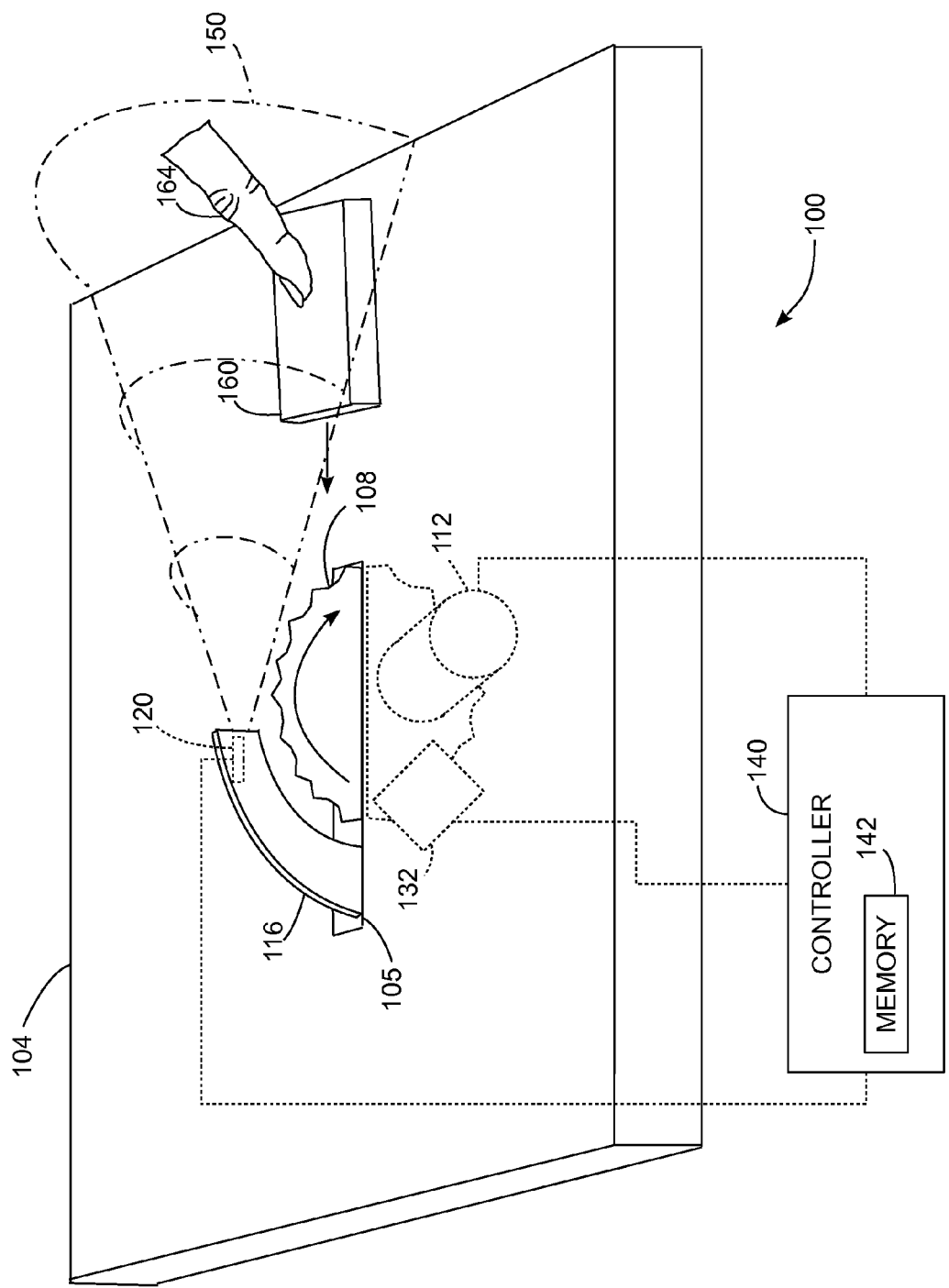
FIG. 1 is a schematic diagram of a table saw with a light sensor that detects the presence of human skin in proximity to a moving saw blade.

FIG. 1 depicts a table saw 100. The table saw 100 includes a table 104 including an opening 105 through which a saw blade 108 extends for cutting work pieces, such as pieces of wood. The table saw 100 also includes an electric motor 112, riving knife 116, light sensor 120, implement arrest mechanism that is embodied as a blade brake 132, and controller 140. The general configuration of the table 104, blade 108, and motor 112 are well known to the art for use in cutting work pieces and are not described in greater detail herein. Additionally, riving knives similar to the riving knife 116 are known to the art, but existing riving knives do not incorporate sensors, such as the light sensor 120. Some components that are commonly used in table saws, such as guides for work pieces, blade height adjustment mechanisms, and blade guards are omitted from FIG. 1 for clarity.

In the saw 100, the light sensor 120 is mounted to the riving knife 116 above a portion of the saw blade 108. The light sensor 120 includes infrared emitters and an infrared detector that is depicted in more detail below. The light sensor 120 generates image data of objects in a region 150 that extends from the riving knife 116. The region 150 is approximately conical in shape and extends along the length of the saw blade 108 over the table 104. In the saw 100, the riving knife 116 is located at a predetermined distance from the saw blade 100, and the riving knife 116 moves with the saw blade 108 as the saw blade 108 is adjusted during operation.

The controller 140 is operatively connected to the motor 112, light sensor 120, and a brake 132. The controller 140 includes one or more digital logic devices including general purpose central processing units (CPUs), microcontrollers, field programmable gate arrays (FPGAs), application specific integrated circuits (ASICs) and any other digital logic devices that are suitable for operation of the saw 100. The controller 140 includes a memory 142 that stores programmed instructions for the operation of the controller 140, and optionally stores data received from the light sensor 120. In one configuration, the memory 142 stores reflectance data for one or more objects in the region 150 to track the direction of movement and rate of movement of the objects over time.

During operation, the controller 140 receives data from the light sensor 120 corresponding to reflectivity of one or more objects in the region 150 to emitted light in one or more wavelengths. As described in more detail below, the controller 140 deactivates the motor 112 and operates the brake 132 if the data received from the light sensor 120 indicate that an appendage or other part of a human operator is at a predetermined target location that is near the blade 108. The brake 132 is an example of an implement arrest mechanism that stops the movement of the blade 108 in a rapid manner. In another embodiment, the saw 100 includes a blade retraction mechanism that pulls the blade 108 beneath the level of the table 104 to prevent contact between the finger 164 and the moving blade.

During operation, the motor 112 rotates the saw blade 108 as indicated in FIG. 1. An operator moves one or more work pieces, such as a piece of wood 160, toward the rotating blade 108 for cutting. A human operator typically pushes the work piece with an appendage, such as a finger 164 depicted in FIG. 1, or one or more hands. The light sensor 120 generates infrared reflectivity data corresponding to both the wood work piece 160 and the finger 164. As described below, the controller 140 distinguishes between the block 160 and the finger 164 based on the different propensities of the wood block 160 and the finger 164 to reflect infrared radiation in different wavelengths. If the finger 164 remains beyond a predetermined distance from the blade 108 and if the rate at which the finger 164 approaches the blade 108 remains sufficiently low, the motor 112 continues to rotate the blade 108 as the work piece 160 contacts the blade 108 for cutting.

While FIG. 1 depicts a table saw as an illustrative example of a power tool, alternative embodiments incorporate the light sensor 120 in a wide range of power tools including, but not limited to, handheld electric drills, drill presses, handheld circular saws, reciprocating saws, band saws, routers, grinders, and any other power tool with a moving implement. In the alternative embodiments, one or more light sensors are mounted on the housings or supports of the various power tools to enable monitoring of a region proximate to the implement where a hand or other part of a human may approach the implement during operation.

Figure 2:
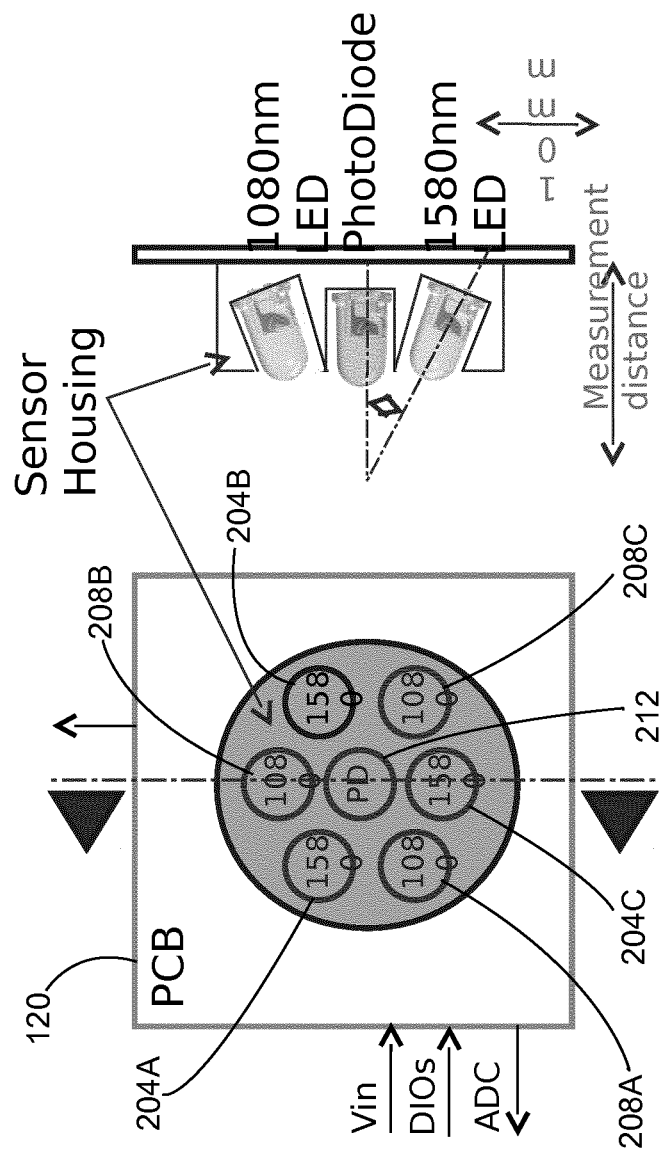
FIG. 2 is a schematic diagram of the light sensor in the saw of FIG. 1.

FIG. 2 depicts the sensor 120 in more detail. The sensor 120 includes two arrays of emitters produce infrared radiation at two different wavelengths. In the embodiment of FIG. 2, the emitters are light emitting diodes (LEDs) that emit infrared radiation at wavelengths of 1080 nm for the LEDs 204A-204C, and at 1580 nm for the LEDs 208A-208C. The sensors 120 includes a photodetector 212 that receives reflected infrared signals from objects that reflect the infrared radiation from the emitters 204A-204C and 208A-208C. The photodetector 120 is, for example, a photodiode, a charge coupled device (CCD), complementary metal-oxide semiconductor (CMOS), or any other detector that is configured to detect the level of reflected light at wavelengths corresponding to the wavelengths of the emitters 204A-204C and 208A-208C. During operation, the sensor 120 activates the emitters 204A-204C and 208A-208C in an alternating sequence so that the sensor 120 only emits the 1080 nm or 1580 nm infrared radiation at any one time during operation. In alternative embodiments of the sensor 120 that include additional light emitters at different wavelengths, the controller 140 operates multiple emitters at different times using a time division multiplexing technique to detect reflectance levels for one or more objects. For example the controller 140 operates a light sensor that includes multiple LEDs that emit light at approximately 540 nm, 660 nm, 860 nm, 1080 nm, and 1580 nm wavelengths with each of the emitters being operated at different times to enable the light sensor 120 to detect the reflectance levels for each wavelength individually.

Figure 3:
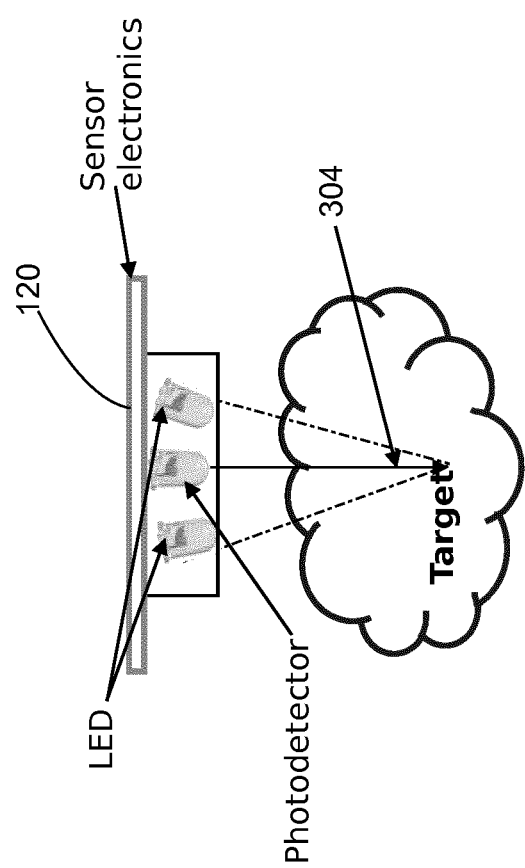
FIG. 3 is a diagram depicting the light sensor directing light to a target object.

The photodetector 212 detects samples of the reflected infrared radiation at different times to generate reflectivity measurements for both wavelengths. In the configuration of FIG. 2, the emitters 204A-204C and 208A-208C are arranged in a circular configuration around the photodetector 212. As depicted in FIG. 3, the LED emitters 204A-204C and 208A-208C in the sensor 120 are aligned at a predetermined angle to converge upon a target 304 at a predetermined distance from the photodetector 212. In the saw 100, the sensor 120 views a target that is in a location near the saw blade 108. When the target is a work piece, then the saw 100 continues operation. If, however, the saw motor 112 is activated and the target is a finger, hand, or other human body part, then the controller 140 activates the blade brake 132 or a blade drop mechanism to prevent contact between the moving blade 108 and the human body part.

Figure 4:
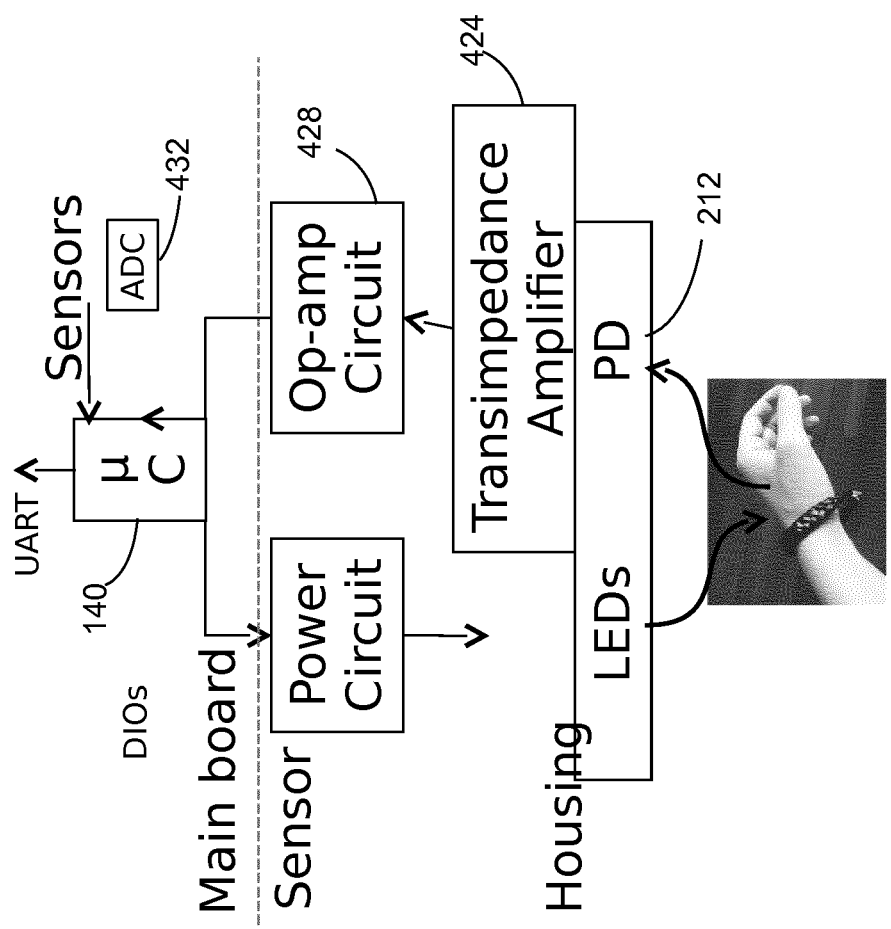
FIG. 4 is a schematic diagram of components in the sensor and the saw of FIG. 1.

FIG. 4 depicts a schematic diagram of selected components in the sensor 120. The sensor 120 generates an output voltage signal from the photodetector 112 using a transimpedance amplifier 424, and generates an analog voltage output with an operational amplifier 428. An analog to digital converter (ADC) 432 converts the analog signals into digital data and the digital controller 140 receives the digital data for use in identification of human body parts in the field of view of the sensor 120.

During operation, the controller 140 receives image data from the sensor 120. In one embodiment, the image data can include a single pixel corresponding to a small target location that reflects infrared radiation from the emitters 204A-204C and 208A-208C. In another embodiment, the sensor 120 generates two-dimensional image data with an array of pixels in a similar manner to a digital camera. The two-dimensional image data depicted reflected light from different objects in a scene in front of the sensor 120. In the saw 100, the controller 140 generates at least two images corresponding to the scene when the scene is illuminated with the 1080 nm wavelength radiation in one image and when illuminated with the 1580 nm wavelength radiation in another image.

In the system 100, the controller 140 identifies objects in the image data from the sensor 120 that correspond to human skin while ignoring other objects, including work pieces that the saw 100 cuts during operation. In the standard visible spectrum, human skin has a range of complexion tones, and many of the tones could be confused with non-human objects. In the infrared spectrum, however, human skin has a relatively high reflectance level in a range of wavelengths from approximately 800 nm to 1100 nm, and a relatively low reflectance level in an infrared band with wavelengths longer than 1400 nm. The high reflectivity in the 800 nm-1100 nm band occurs regardless of the skin tone of the human in the visible spectrum, and is believed to be due at least in part to the presence of melanin in human skin. As is known in the art, water has a high rate of absorption near the 1400 nm wavelength, and human skin tends to have low reflectivity to the range of wavelengths near 1400 nm because human skin has a high level of water content.

Figure 5:
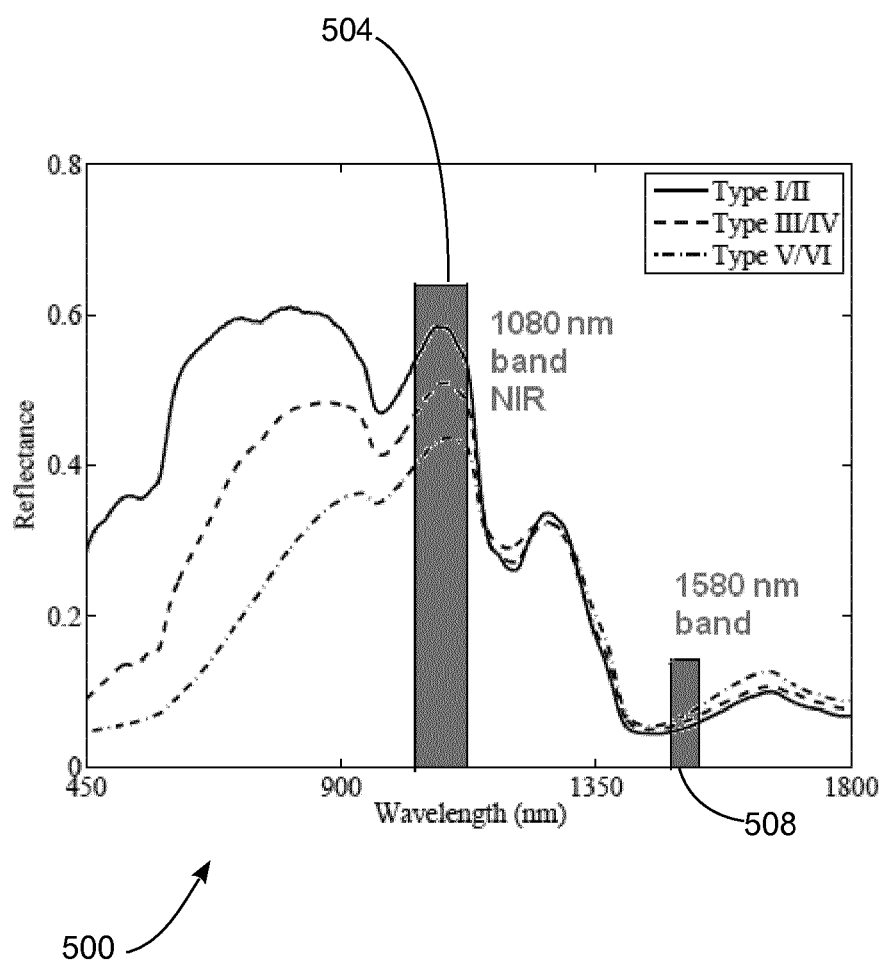
FIG. 5 is a graph depicting the reflectance levels of human skin to different wavelengths of light.

FIG. 5 depicts a graph 500 of the reflectance levels for different skin tones (Type I-Type VI) in the infrared spectrum. In the graph 500, the 1080 nm wavelength 504 has a high reflectance level for all the skin tones, while the 1580 nm wavelength 508 has a low reflectance level for all the skin tones. FIG. 5 depicts a range of wavelengths from approximately 1350 nm to 1800 nm where the infrared reflectivity of human skin is substantially lower than the reflectance levels in the 800 nm to 1100 nm range of wavelengths.

In the saw 100, the controller 140 uses the image data for both the 1080 nm and 1580 nm wavelengths to identify a Normalized Differenced Skin Index (NDSI) parameter for one or more objects in the image data based on a reflectance parameter $\hat{\rho}$ at different wavelengths. The NDSI $\gamma$ is provided by the following equation:

$$\gamma = \frac{\hat{\rho}(1080 \text{ nm}) - \hat{\rho}(1580 \text{ nm})}{\hat{\rho}(1080 \text{ nm}) + \hat{\rho}(1580 \text{ nm})}.$$

The reflectance parameter $\hat{\rho}$ refers to the ratio of power of source emitter to the reflected power as detected by the photo detector. Thus, the NDSI term $\gamma$ corresponds to a difference between the reflectance levels of an object at two different wavelengths. In the case of human skin, the shorter wavelength at 1080 nm produces a higher level of reflection, which the longer wavelength at 1580 nm produces a lower level of reflection. In some embodiments, the controller 140 also uses additional spectral parameters including the Normalized Differenced Red-Green Index (NDGRI) and the Normalized Differenced Vegetation Index (NDVI) to distinguish between human skin and various objects, including dirt, rocks, and vegetation. The NDGRI parameter is measured in a similar manner to the NDSI parameter but measures reflectance levels at different light wavelengths as set for the in the following equation:

$$\beta = \frac{\hat{\rho}(540 \text{ nm}) - \hat{\rho}(660 \text{ nm})}{\hat{\rho}(540 \text{ nm}) + \hat{\rho}(660 \text{ nm})},$$

where the 660 nm wavelength corresponds to red light and the 540 nm wavelength corresponds to green light, although alternative embodiments may employ different wavelengths to identify the NDGRI. Similarly, the NDVI parameter is identified using two different light wavelengths that are set forth in the following equation:

$$\alpha = \frac{\hat{\rho}(860 \text{ nm}) - \hat{\rho}(660 \text{ nm})}{\hat{\rho}(860 \text{ nm}) + \hat{\rho}(660 \text{ nm})}.$$

The general NDSI, NDGRI, and NDVI parameters are known to the art and are disclosed in "A Physical Model of Human Skin and Its Application for Search and Rescue," by Maj. Abel S. Nunez. Table 1 depicts a set of common materials with corresponding NDSI and NDGRI parameters.

TABLE 1

| Material | NDVI | NDSI | NDGRI |
|---|---|---|---|
| Fair Skin | 0.04 | 0.77 | −0.25 |
| Darkly Pigmented Skin | 0.51 | 0.66 | −0.34 |
| Grass | 0.88 | 0.53 | 0.37 |
| Leaf | 0.9 | 0.27 | 0.41 |
| Plastic Doll | 0.04 | 0.24 | −0.28 |
| Paper bag | 0.27 | 0.15 | −0.27 |
| Cardboard | 0.3 | 0.14 | −0.33 |
| Red | −0.01 | −0.01 | −0.47 |
| Soil | 0.37 | −0.1 | −0.18 |

Figure 6:
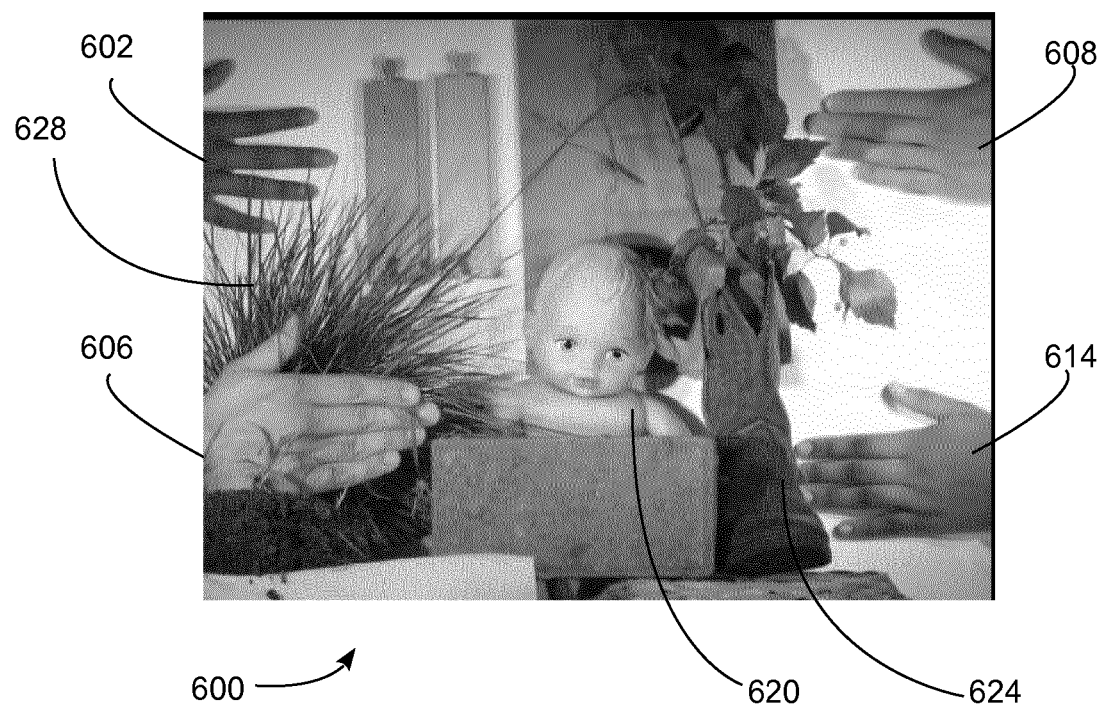
FIG. 6 is a set of photographs depicting a scene in the visual spectrum and in the infrared spectrum after application of a normalized difference skin index (NDSI) and thresholding process to two infrared images.
Figure 6:

In the saw 100, the memory 142 stores a predetermined set of parameter data for one or more of the NDSI, NDVI, and NDGRI parameters for human skin and optionally for other materials that the light sensor 120 detects during operation of the saw 100. The controller 140 uses one or more of the NDVI, NDSI, and NGRI metrics to identify if the image data from the sensor 120 corresponds to the skin of a human operator or to another object. The different index values enable the controller 140 to distinguish between objects even if the objects have a similar visual appearance to skin. For example, FIG. 6 depicts a scene in a visible image 600 and a corresponding image 650 that depicts the NDSI of pixels in the image using two images of the scene taken at the 1080 nm and 1580 nm wavelengths. The scene 600 includes four visible hands 602, 606, 608, and 612. The scene 600 also includes several other objects that are not part of a human body. In particular, the scene 600 includes a doll 620 that visually approximates human skin, a leather boot 624 that is formed from animal hide, and grass 628. The image 650 depicts the scene of the image 600 using the NDSI values for each pixel in two different images taken at the 1080 nm and 1580 nm wavelengths. The image 650 is a binary thresholded image, where any pixel with an NDSI parameter level that is below a predetermined NDSI threshold is depicted as a white pixel and pixels that exceed the NDSI threshold are depicted as black pixels. In the illustrative example of FIG. 6 the NDSI threshold parameter is selected as $\gamma_T=0.6$. Using the threshold, the image 650 includes the visible hands 652, 656, 658, and 664 that correspond to the hands 602, 606, 608, and 614, respectively, in the image 600. The rest of the scene remains white because the NDSI parameters for the other objects in the scene are all below the predetermined NDSI threshold level $\gamma_T$.

In some power tool embodiments, the sensor 120 also includes LEDs or other light emitting elements that produce light at wavelengths suitable for identification of one or both of the NDGRI and NDVI parameters. For example, the sensor 120 detects reflected light from light emitters that generate wavelengths of approximately 540 nm and 660 nm to identify the NDGRI parameter. In one embodiment, the sensor 120 includes at least two additional LEDs or other light emitting elements that produce light in a wavelength range of approximately 500-600 nm and 600-700 nm for detection of two reflectance levels in the NDGRI parameter. The sensor 120 detects reflected light from light emitters that generate wavelengths of approximately 660 nm and 860 nm to identify the NDVI parameter. In one embodiment, the sensor 120 includes at least two additional LEDs or other light emitting elements that produce light in a wavelength range of approximately 600-700 nm and 800-900 nm for detection of two reflectance levels in the NDVI parameter. While the illustrative embodiments of the sensor 120 use multiple LEDs with different emission wavelengths to illuminate a region around the saw blade 108, an alternative embodiment uses a single illumination source that is reconfigurable to emit light at each of the different wavelengths required for generation of the NDSI, NDGRI, and NDVI parameters based on the reflectance levels of light at the different wavelengths. The controller 140 optionally operates the single light source using a time-division multiplexed operating mode to change the wavelength of emitted light from the single light source at a predetermined rate.

In the saw 100, the controller 140 uses a predetermined threshold and compares the identified NDSI level of the image data from the sensor 120 to identify if the target is an object with an NDSI level below a predetermined threshold or the skin of a human operator with an NDSI level that exceeds the threshold. As described, above, if the saw 100 is in operation when the controller 140 detects the human skin, and if the object is within a predetermined distance of the implement or is moving toward the implement at greater than a predetermined rate, then the controller 140 activates the implement arrest mechanism, such as the blade brake 132 or a blade retraction mechanism, to prevent contact between the human operator and the moving saw blade 108.

Figure 7:
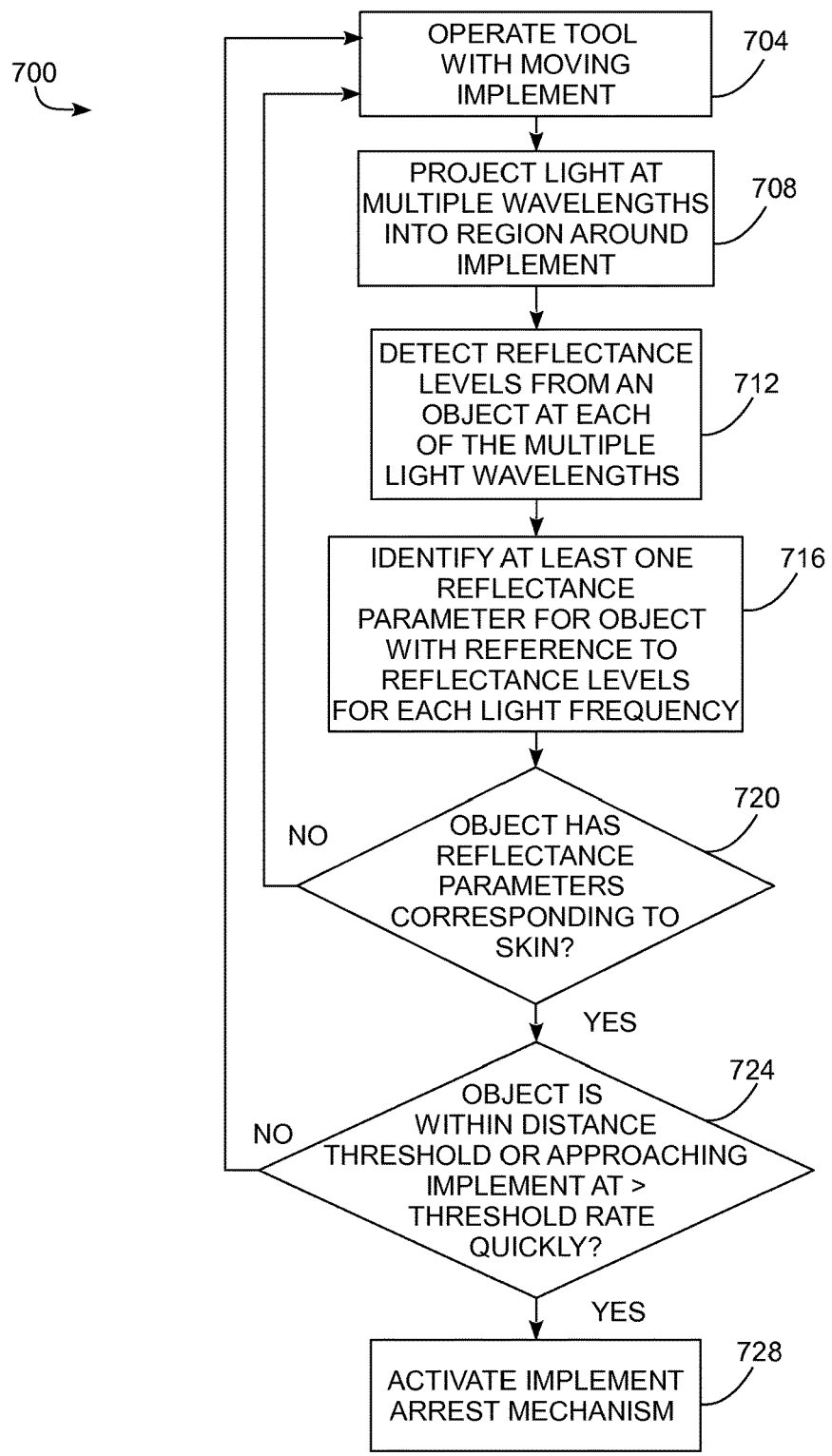
FIG. 7 is a flowchart illustrating an exemplary process of operating the saw of FIG. 1.

FIG. 7 depicts a process 700 for the operation of a power tool with a moving implement to detect human skin on an object in a region around the moving implement and activated an implement arrest mechanism if the object moves within a predetermined distance of the implement or is moving toward the implement at greater than a predetermined rate. In the discussion below, a reference to the process 700 performing a function or action refers to the execution of stored program instructions in a controller to perform the function or action in conjunction with other components in the power tool. The process 700 is described in conjunction with the table saw 100 of FIG. 1 for illustrative purposes.

Process 700 begins as the controller 140 operates the motor 112 to move an implement, such as the saw blade 108 in the example of the saw 100 (block 704). During operation of the saw 100, the saw blade 108 cuts one or more work pieces, such as a piece of wood a piece of wood 160.

During operation of the saw 100, the light emitting elements in the sensor 120 emit light at multiple wavelengths into the region 150 that is located around the blade 108 above the surface of the table 104 in the saw 100 (block 708). As described above in FIG. 2, the light sensor 120 mounted on the riving knife 116 includes photodiodes that emit light at multiple wavelengths. The photodetector in the light sensor 120 detects reflected light at the different wavelengths from one or more objects in the field of view of the sensor 120 (block 712). For example, in FIG. 1 the light sensor 120 detects the reflectance levels of light from the piece of wood 160 and optionally from the finger 164.

Process 700 continues as the controller 140 identifies at least one reflectance parameter value based on the reflectance levels from an object in the field of view of the sensor 120 (block 716). As described above, the controller 140 identifies one or more of the NDSI, NDGRI, and NDVI parameters based on the reflectance values from the object and identifies if one or more of the parameters correspond to human skin based on the predetermined reflectance parameter data that are stored in the memory 142. In one embodiment, the controller 140 identifies the NDSI with reference to two measured reflectance levels for light that is emitted in the 800 nm to 1100 nm range and light that is emitted in the 1350 nm and 1800 nm range.

During process 700, the controller 140 identifies if the reflectance parameters for an object in the field of view of the light sensor 120 correspond to human skin (block 720). If the NDSI value for an object exceeds a predetermined threshold, such as 0.6 in the illustrative example of Table 1, then the controller 140 identifies skin, which indicates that the object is part of a human body. In some embodiments, the controller 140 also identifies the NDVI parameter with reference to two measured reflectance values for light that is emitted in the 600 nm to 700 nm range and light that is emitted in the 800 nm to 900 nm range. In some embodiments, the controller 140 also identifies the NDGRI parameter with reference to two measured reflectance values for light that is emitted in the 500 nm to 600 nm range and light that is emitted in the 600 nm to 700 nm range. In one configuration, the controller 140 uses either or both of the identified NDVI and NDGRI parameter values to reduce the probability of a false-positive reading for the NDSI parameter. For example, the controller 140 identifies that the NDVI parameter value is less than a first predetermined threshold (e.g. 0.6 based on the table of FIG. 1) and that the NDGRI parameter is less than a second predetermined threshold (e.g. −0.15 based on the table of FIG. 1) to confirm that the reflectance levels of the object correspond to skin when the NDSI level exceeds the predetermined threshold.

During the process 700, the saw 100 continues operation if the controller 140 does not identify an object with reflectance parameter values that correspond to human skin (block 720), and process 700 returns the processing that is described with reference to block 704. If, however, the controller 140 identifies that an object in the field of view of the sensor 120 has reflectance levels that correspond to human skin during the processing of block 720, then the controller 140 further identifies if the object is either within a predetermined distance of the saw blade 108 or is moving at greater than a maximum predetermined velocity (block 724). In some embodiments, the light sensor 120 is positioned with a field of view around the blade where any detection of human skin is within a minimum distance of the blade 108, and the controller 140 activates the blade arrest mechanism 132 in response to detecting the object with reflectance values that correspond to human skin (block 728). In other embodiments, the light sensor 120 tracks either or both of the distance between the object and the saw blade 108 and a velocity of the object. The saw 100 continues operation (block 704) as long as the distance between the object and the saw blade 108 remains greater than a first predetermined threshold and the velocity of the object remains below a second predetermined threshold. For example, in one embodiment the controller 140 continues operation of the saw 100 as long as the detected object, such as the finger 164, remains more than 20 cm from the blade and the velocity of the finger 164 remains below 10 cm/sec moving toward the blade 108. If, however, the finger 164 either moves within the predetermined distance threshold or exceeds the predetermined maximum velocity moving toward the blade 108, then the controller 140 activates the blade arrest mechanism (block 728).

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the following embodiments.

What is claimed:

1. A method of operating a power tool comprising:
   operating an actuator to move an implement;
   activating with a controller only a first emitter to emit light at a wavelength between 800 nm and 1100 nm;
   identifying with the controller a first reflectance level from an object with reference to a first reflection signal received by a photodetector when only the first emitter is activated;
   activating with the controller only a second emitter to emit light at a wavelength between 1350 nm and 1800 nm;
   identifying with the controller a second reflectance level from an object with reference to a first reflection signal received by the photodetector when only the second emitter is activated;
   activating with the controller only a third emitter to emit light at a wavelength between 500 nm and 600 nm;
   identifying with the controller a third reflectance level from the object with reference to a third reflection signal received by the photodetector when only the third emitter is activated;
   activating with the controller only a fourth emitter configured to emit light at a wavelength between 600 nm and 700 nm;
   identifying with the controller a fourth reflectance level from the object with reference to a fourth reflection signal received by the photodetector when only the fourth emitter is activated; and
   activating with the controller an implement arrest mechanism to prevent contact between the object and the implement while the implement is in motion in response to a first ratio corresponding to the first identified reflectance level and the second identified reflectance level exceeding a first predetermined threshold and a second ratio corresponding to the third identified reflectance level and the fourth identified reflectance level being below a second predetermined threshold.

2. The method of claim 1, the activation of the implement arrest mechanism further comprising:
   activating with the controller the implement arrest mechanism to retract a saw blade below a surface of a table in a table saw.

3. The method of claim 1, further comprising:
   identifying with the controller the first ratio as a normalized differenced skin index (NDSI) parameter; and
   activating with the controller the implement arrest mechanism in response to the NDSI parameter exceeding the first predetermined threshold.

4. The method of claim 1 further comprising:
   identifying with the controller the first ratio as a normalized differenced skin index (NDSI) parameter;
   identifying with the controller the second ratio as a normalized differenced red-green index (NDGRI) parameter; and
   activating with the controller the implement arrest mechanism in response to the NDSI parameter exceeding the first predetermined threshold and the NDGRI parameter being below the second predetermined threshold.

5. The method of claim 4 further comprising:
   activating with the controller only a fifth emitter to emit light at a wavelength between 800 nm and 900 nm;
   identifying with the controller a fifth reflectance level from the object with reference to a fifth reflection signal received by the photodetector when only the fifth emitter is activated;

identifying with the controller a normalized differenced vegetation index (NDVI) parameter for the object with reference to the fourth reflectance level and the fifth reflectance level; and activating with the controller the implement arrest mechanism in response to the NDSI parameter exceeding the first predetermined threshold, the NDGRI parameter being below the second predetermined threshold, and the NDVI parameter being below a third predetermined threshold.

6. The method of claim 1 further comprising:

identifying with the controller a distance between the object and the moving implement with reference to the first reflection signal and the second reflection signal; and activating with the controller the implement arrest mechanism in response to the identified distance being less than a predetermined threshold.

7. The method of claim 1 further comprising:

identifying with the controller a velocity of the object with reference to the first reflection signal and the second reflection signal; and activating with the controller the implement arrest mechanism in response to the identified velocity being greater than another predetermined threshold.

8. A method of operating a power tool comprising:

operating an actuator to move an implement;

activating with a controller only a first emitter to emit light at a wavelength between 800 nm and 1100 nm;

identifying with the controller a first reflectance level from an object with reference to a first reflection signal received by a photodetector when only the first emitter is activated;

activating with the controller only a second emitter to emit light at a wavelength between 1350 nm and 800 nm;

identifying with the controller a second reflectance level from an object with reference to a first reflection signal received by the photodetector when only the second emitter is activated;

activating with the controller only a third emitter to emit light at a wavelength between 600 nm and 700 nm;

identifying with the controller a third reflectance level from the object with reference to a third reflection signal received by the photodetector when only the third emitter is activated;

activating with the controller only a fourth emitter configured to emit light at a wavelength between 800 nm and 900 nm;

identifying with the controller a fourth reflectance level from the object with reference to a fourth reflection signal received by the photodetector when only the fourth emitter is activated;

identifying with the controller a first ratio as a normalized differenced skin index (NDSI) parameter for the object with reference to the first reflectance level and the second reflectance level;

identifying with the controller a second ratio as a normalized differenced vegetation index (NDVI) parameter for the object with reference to the third reflectance level and the fourth reflectance level; and activating with the controller an implement arrest mechanism to prevent contact between the object and the implement while the implement is in motion in response to the NDSI parameter exceeding a first predetermined threshold and the NDVI parameter being below a second predetermined threshold.

* * * * *

UNITED STATES PATENT AND TRADEMARK OFFICE
CERTIFICATE OF CORRECTION

PATENT NO. : 10,160,080 B2
APPLICATION NO. : 15/104079
DATED : December 25, 2018
INVENTOR(S) : Ramaswamy et al.

It is certified that error appears in the above-identified patent and that said Letters Patent is hereby corrected as shown below:

In the Claims

In Column 12, Lines 1-3, Lines 9-11 of Claim 8 should read:
activating with the controller only a second emitter to
    emit light at a wavelength between 1350 nm and 1800
    nm Signed and Sealed this
Fourteenth Day of May, 2019

Andrei Iancu
*Director of the United States Patent and Trademark Office*